United States Patent [19]

Charpak et al.

[11] 4,286,158

[45] Aug. 25, 1981

[54] NEUTRAL RADIATION DETECTION AND LOCALIZATION

[75] Inventors: Georges Charpak, Paris; Hoan N. Ngoc, Verrieres le Buisson, both of France; Armando Policarpo, Coimbra, Portugal

[73] Assignee: Agence Nationale de Valorisation de la Recherche (ANVAR), France

[21] Appl. No.: 63,138

[22] PCT Filed: Dec. 7, 1978

[86] PCT No.: PCT/FR78/00046

§ 371 Date: Aug. 2, 1979

§ 102 (e) Date: Aug. 2, 1979

[87] PCT Pub. No.: WO79/00353

PCT Pub. Date: Jun. 28, 1979

[30] Foreign Application Priority Data

Dec. 7, 1977 [FR] France ................. 77 36893

[51] Int. Cl.³ ............ G01T 1/18; H01J 39/29
[52] U.S. Cl. ............................ 250/374; 250/385; 250/484
[58] Field of Search ............... 250/374, 375, 379, 385, 250/388, 363 S, 366, 484

[56] References Cited

U.S. PATENT DOCUMENTS

| | | | |
|---|---|---|---|
| 2,796,527 | 6/1957 | Oosterkamp et al. | 250/366 |
| 2,953,702 | 9/1960 | Zieler | 250/374 |
| 3,786,270 | 1/1974 | Borkowski et al. | 250/374 |
| 4,074,135 | 2/1978 | Stevens | 250/363 S |

Primary Examiner—Alfred E. Smith
Assistant Examiner—Janice A. Howell
Attorney, Agent, or Firm—Larson, Taylor and Hinds

[57] ABSTRACT

A device for detecting and localizing soft gamma and X radiations, comprising an enclosure 10 provided with a window 11 opaque to light and transparent to incident radiations, occupied by a noble gas and provided with electrodes for causing the electrons to drift towards a secondary photon creation space.

In said space there reigns an electric field having sufficient value to cause the formation of secondary photons by excitation then de-excitation of the atoms of the noble gas. The secondary photons pass through a transparent window 12 and are converted into photons in the close UV or visible spectrum. The scintillations are localized by PM tubes 23 and 24.

9 Claims, 5 Drawing Figures

U.S. Patent      Aug. 25, 1981      Sheet 1 of 2      4,286,158
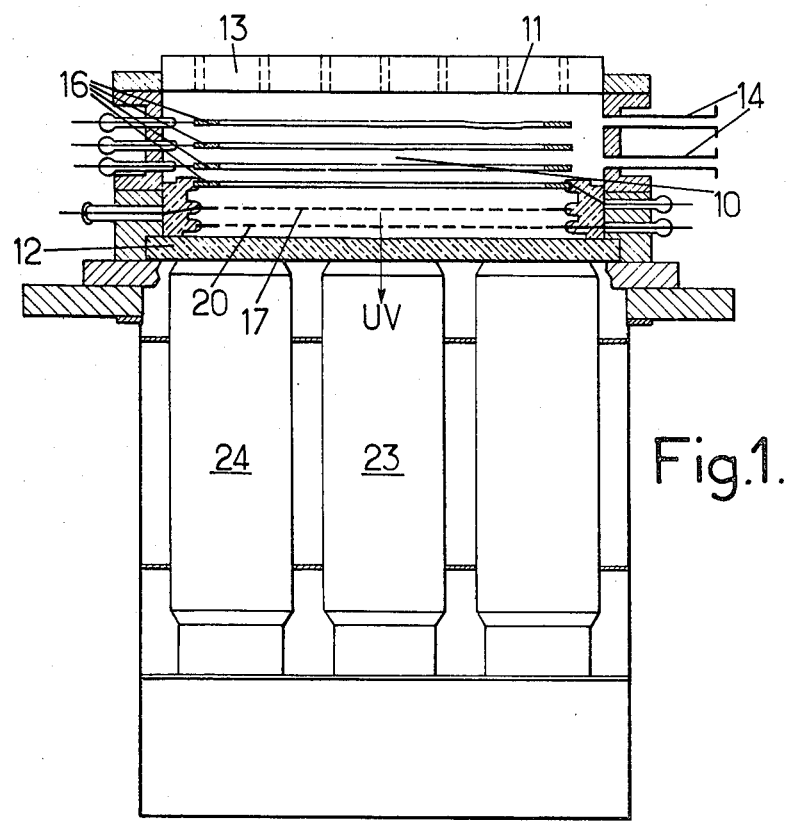
Fig.1.
Fig.2.
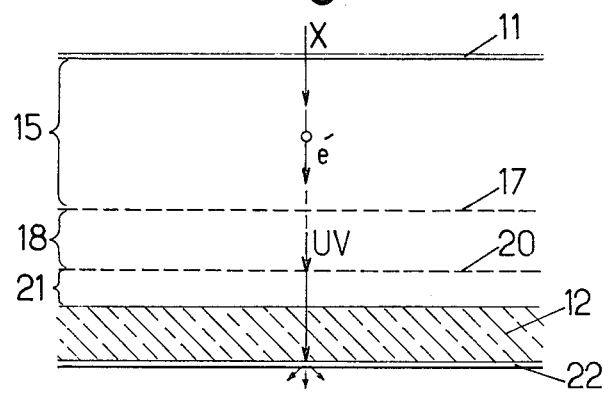

NEUTRAL RADIATION DETECTION AND LOCALIZATION

The present invention concerns the detection and the localization of neutral radiation and particularly soft gamma and X radiation. This application being however not limiting.

Numerous devices are already known for localizing the sources of radiation and supplying a visible image thereof. These devices have a wide application in the medical field where they are particularly used for determining in vivo the distribution in an organ of an element which is either a radio-isotope, or an element emitting X rays by X fluorescence.

The present invention aims at providing a neutral radiation localizing process and device supplying a satisfactory spatial resolution for most medical applications, and an energy resolution which cannot be reached with gas detectors based on proportional counters or scintillation counters. Only solid state detectors may compete in energy resolution but the detector described permits large surfaces to be realized which cannot be attained at moderate prices with solid scintillators, such as those for "gamma cameras."

To this end, the invention proposes particularly a process for the detection and localization of incident neutral radiation, in particular soft gamma and X radiation, in which the formation of photoelectrons is caused by action of incident radiation on the atoms of gas contained in an enclosure, the electrons are drifted by means of an electric field towards a space subjected to an electric field of sufficient value for photons to be created by excitation of gas atoms and return of these atoms to the de-excited condition; the photons are collected through a transparent window on a layer of material for converting said photons into scintillations in the close UV or visible spectrum and the barycenter of the scintillations on the layer is localized, e.g. by means of photomultipliers or ionization detectors.

The invention proposes a detection and loalization device comprising (generally downstream of a collimator having a network of inlet holes) a sealed enclosure provided with an inlet window transparent to the incident radiation, occupied by a gas supplying, by interaction with the incident radiation, photoelectrons, and provided with electrodes for creating an electric field for causing the electrons to drift towards a space of creation of secondary photons. This space will in general be delimited, in said enclosure, by electric field creation electrodes of a sufficient value to induce the formation of secondary photons, in general in the far ultraviolet, by excitation of the gas atoms which occupy the enclosure and return of these atoms to the de-excited condition.

The secondary photons pass through an outlet window associated with means for localizing the origin of these secondary photons. These origin localization means may be formed by a layer of material for converting the photons into scintillations in the close ultra-violet or in the visible spectrum and photomultipliers disposed in a regular network opposite the layer, associated with an analog or digital computing circuit using for example microprocessors.

For gamma radiation energy greater than 20 keV, the primary scintillation, created by the photoelectron produced during absorption of the γ radiation, is sufficiently intense to be detected by the photomultipliers. Then two signals are available: the primary instantaneous signal and the delayed signal produced during the passage of ionization electrons through the secondary photon creation space. The time which separates the two signals is proportional to the distance travelled by the ionization electrons and so gives the depth of the absorption point of the neutral radiation.

This is very important for the applications where the neutral radiation emanates from a point: this case is that of so-called pin-hole cameras, or of the diffraction of γ or neutron rays, for example by means of small-size crystals.

In the case of slow neutron sources, the gas could be helium 3 which is well suited, as all the noble gases, to the phenomenon of stimulated emission by the electric field. In this case, the primary scintillation would be particularly easy to detect because of the high energy of the recession nucleii produced by absorption of the neutron. The measurement of the time separating the primary scintillation from the delayed stimulated scintillation renders unnecessary the presence of electrodes producing cylindrical or spherical potentials.

The spaces for creating photoelectrons, drifting and forming secondary protons, will in general be occupied by at least one noble gas, the composition and the pressure of the atmosphere of these spaces being chosen with regard to the energy of the incident radiation. By way of example, xenon may be used in the enclosure assembly, at a pressure of 1 atmosphere for detecting X radiation from 6 to 50 keV; xenon at 5 atmospheres if the energy is between 1 and 30 keV. The thickness of the photoelectron formation space obviously plays a role in the absorption of incident radiation. In practice, a value between 5 and 20 cm will in general be selected.

The invention will be better understood from reading the following description of a device which forms one particular embodiment thereof given by way of a non limiting example. The description refers to the accompanying drawings in which:

FIG. 1 is a simplified diagram of the device, in section along a plane passing through its axis;

FIG. 2 is an enlarged schematic diagram for explaining the operation of the device;

Figure 4:
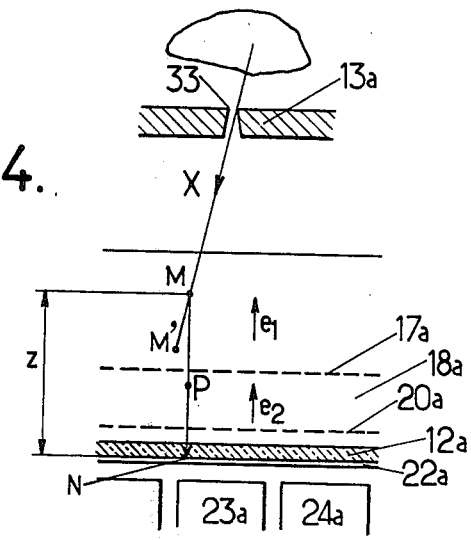
Figure 5:
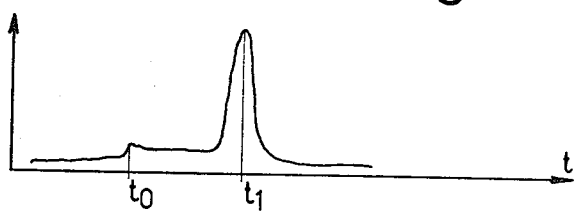

FIG. 4, similar to FIG. 1, shows another embodiment;

FIG. 5 shows schematically (the scale not being respected) the spacing out in time of the primary and secondary scintillations due to the same radiation.

The device shown in FIG. 1 may be considered as being formed of two distinct parts, the first being for the formation of secondary photons and the second part for localizing formation points.

The first part comprises a sealed enclosure 10 which, in the embodiment shown, comprises a sidewall formed from stacked rings fixed sealingly to each other, an inlet window 11 and an outlet window 12. Inlet window 11 is made from a material opaque to light, having a thickness and an atomic number sufficiently small to be transparent to incident radiation (X radiation for example). This inlet window may be made from a plastic material (mylar for example) or from a light alloy. If the enclosure is occupied by a pressurized gas, the inlet window 11 will obviously have to have a thickness sufficient to withstand the forces which are exerted thereon. In practice however, the appearance of excessive stresses in the inlet window 11 may be avoided by supporting it against the collimator 13, formed by a thick plate provided with parallel or convergent through holes, which is anyhow necessary in most cases.

During operation, there must be maintained in the enclosure a dry atmosphere of noble gas whose composition and pressure are selected depending on the energy of the radiation to be detected. For this purpose, one of the rings forming the sidewall of the enclosure is provided with connections 14 for connecting to a closed circuit (not shown) comprising an oven heated to a temperature between 400° C. and 700° C., a gas cooling exchanger at the outlet of the oven and a circulating pump. The oven is occupied by a reducer (calcium in shavings for example) and maintained at a temperature sufficient for achieving the required purification. With this closed circuit is associated a reserve gas cylinder.

The enclosure is divided, by means of electrodes highly transparent to the neutral and the electrons, into three successive spaces.

A first space forms a photoelectron creation chamber and a drift chamber. This first space, referenced 15 in FIG. 2, has a thickness sufficient to convert an important fraction of the incident neutral radiation into photoelectrons. In practice, its thickness will in general be a few centimeters. It is subjected to a weak electric field, from 1 to a few hundred volts per centimeter, for causing the photoelectrons and the additional electrons which they produce by ionization, to drift towards the second space. In the embodiment shown in FIG. 1, these electrodes comprise a first electrode formed by the inlet window 11 itself (whose rear face is metallized if it is made from an insulating material), connected to earth potential, then annular electrodes 16 connected to successive staggered potentials and, finally, a high vacuum rate grid 17.

The second space, referenced 18 in FIG. 2, is intended to induce the creation of radiations in the distant ultra-violet spectrum by excitation of the neutral atoms of the gas which occupies the enclosure assembly 10, then de-excitation of these atoms. The electrical field, formed between electrodes 17 and 20 which define the second space, must be sufficient for there to be excitation of the neutral atoms, but sufficiently small to avoid the appearance of permanent ionization. In practice, an electric field of a few kilovolts per centimeter will be used.

Finally, a third space (21 in FIG. 2) is defined by electrode 20 and outlet window 12. Space 21 is advantageously subjected to a weak electric field, in a direction opposite that which reigns in space 18, to prevent electrons passing through space 18 from striking window 12. This electrical field may be created between electrode 20 and a transparent metal coating on the internal face of window 12.

Window 12 is made from a material transparent to the distant ultraviolet radiation created in space 18, generally from quartz. The UV photons coming from space 18 and which have passed through space 20, strike a thin layer of frequency converter material 22 covering the external face of the window. This material, formed in general by an aromatic substance such as P-terphenyl or P-quarterphenyl converts the distant UV photons into photons in the near UV or visible range. In the embodiment shown in FIG. 2, the layer is placed on the external face of the window. It will be noted in passing that this outlet window may be much thinner than the scintillating crystal of a gamma camera and that it does not then cause a comparable loss of resolution.

The converter material layer may be considered as the inlet member of the second part of the device, intended for localization purposes. This second part comprises several photomultiplier tubes spread out evenly opposite the outlet window, so as to observe the scintillations in the layer of converter material. In the embodiment shown in FIG. 1, there is provided a central photomultiplier tube 23 surrounded by a ring of photomultipliers 24, to the number of six for example. If a large diameter enclosure is used, an extra external ring may be possibly used. In each case, the number of rings of photomultipliers will be chosen so as to allow an estimate of the barycenter of the radiations emitted with sufficient accuracy.

The photomultipliers are associated with a circuit for estimating the site of emission of the incident neutral radiation. The localization may be carried out by computation of the ratio of the signals supplied by the different photomultiplier tubes 23 and 24.

It is not necessary to describe here a circuit for effecting the localization. In fact, it may be an analog circuit of the type widely used at present in gamma cameras.

In most cases, it will be useful to estimate also the energy of the instant neutral radiation. All that is needed for that is to find the sum of the pulses supplied by all the photomultipliers in response to the same event. The energy resolution which may be obtained, and which allows discrimination to be effected, is much better than that obtained in a wire counter or in an apparatus using a scintillator crystal.

Figure 3:
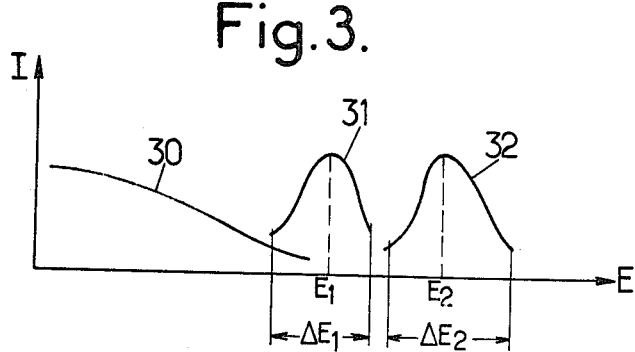
FIG. 3 shows schematically intensity variation I of the radiation due to two radio-isotopes with respect to energy E, close to emission peaks.

The advantages achieved by this improved energy selectivity appear in FIG. 3 in which 30, 31 and 32 designate respectively the representative curves of the emission peaks for first and second radio-isotopes and of the Compton diffusion spectrum due to these isotopes, contained in the source to be studied.

In particular, the image may be discriminated due to the monochromatic radiation coming from the first radio-isotope, of energy $E_1$, from the image coming from the Compton diffusion spectrum. Thus, there may be obtained a sharper and more contrasted representation of the distribution of the radio-isotope in the source.

For that, it is sufficient to apply the output signals of the summator to a multichannel analyzer comprising a simulation window $\Delta E_1$. The output signal of the analyzer is applied to the control input of a gate associated with the localization circuit and only the information corresponding to the energy window is taken into account.

There may also be formed simultaneously the images coming from two radio-isotopes whose radiations have closely related peaks $E_1$ and $E_2$. For that, multichannel analyzers with window $\Delta E_1$ and $\Delta E_2$ (FIG. 3) will again be used.

One important application of this latter mode of using the invention consists in the simultaneous formation of the image of two neighbouring organs having fixed distinct radio-isotopes (liver and pancreas for example).

The advantages provided by the invention appear immediately if one compares the amount of light obtained by ionization of the noble gas in space 15 with that which is obtained in a scintillator crystal. For the same energy loss, the amount of light obtained is about 100 times greater.

Moreover, one obtains a plane resolution which may easily reach 2 mm, whereas 10 mm is scarcely exceeded in the case of a camera using a thick scintillator crystal.

By way of example, the following characteristics may be indicated, which are those for a device intended to detect and to localize X radiations coming from a radio-isotope or from an element excited by fluorescence. Space 15 had a thickness of 5 mm and was subjected to an electrical field of the order of 500 V/cm. Space 18, having a thickness of 7 mm, was delimited by electrodes between which there reigned a potential difference of 4000 V. The layer of converter material was formed by a deposit of P-terphenyl to a thickness of 1000 $\mu$ g/cm$^2$.

The embodiment of the invention shown in FIG. 1 comprises a multihole collimator 13 by means of which only the X or gamma radiations substantially parallel to the axis may penetrate into the photoelectron creation chamber. For a given radiation direction, the coordinates x, y of the point where a scintillation will appear on the converter layer 22 will not depend on the length travelled by the incident radiation in the photoelectron creation chamber before absorption.

It is not the same when, instead of a multi-hole collimator, a pinhole collimator is used. A device incorporating such a collimator is shown in FIG. 4, where the parts corresponding to those of FIG. 1 bear the same reference number, to which the index a is added. According as to whether the conversion of the incident X radiation takes place at M or at M', the plane coordinates x and y of point N where the scintillation will appear will be different.

The invention allows a standardization correction to be effected by determination of z, then application to x and y of a scale factor which is a function of z. For that, it is necessary to measure z. This measure is possible without addition of extra detecting members, to the extent that the X radiation coming from the source (created either by fluorescence or by radio-activity) has an energy greater than a threshold of the order of 10 keV, typically greater than 20 keV.

At point M, and X radiation gives rise to a photoelectron which produces, by ionization of the noble gas, a bunch of electrons which drift along the lines of force of electrical field $e_1$, as far as the creation space 18a of the secondary radiation, then, under the effect of field $e_2$, as far as point P. From the moment that the bunch of electrons is created at M, there is produced a primary luminescence or scintillation in the noble gas. In response to this luminescence, the photomultipliers 23a and 24a supply a signal at a time $t_0$. When the bunch of electrons arrives at point P, it produces a secondary luminescence of an intensity directly proportional to the electrical field $e_2$, at a time $t_1$ (FIG. 5). P will in most cases practically merge with the plane of the grid 17a. The distance z will be the sum of the thickness between 17a and 22a and of the product of $(t_1-t_0)$ by the drift speed of the electrons in the space where the electrical field $e_1$ reigns.

The measurement of x and y will be effected solely by processing the secondary luminescence signal appearing at time $t_1$, much more intense than the first. The correction calculation will be effected in a conventional way, either by analog means or by digital means.

Knowing the coordinates x, y and z of conversion point M in relation to hole 33 of collimator 13a, the exact image may be constituted of the projection of the source through hole 33 onto a given surface, flat for example, by effecting:

the correction of the conversion efficiency with the inclination of the incident ray in relation to the axis of the apparatus, due to the difference of thickness of the gases traversed along the inclination, the projection correction so that an X radiation coming from a point-object only gives an image point.

The invention is capable of numerous embodiments. In particular, instead of using flat electrodes, electrodes for creating a field may be used having a cylindrical symmetry or a symmetry of revolution (as described for example in the French patent application n° 2 363 117. The photomultiplier tubes may be associated, not with an analog computer circuit, but with a digital circuit which has the advantage, especially in the case of a device with a large number of photomultipliers, of allowing much easier balancing.

It will further be noted that the detection of the luminescence induced in the gases of the detectors may take place over the whole electromagnetic spectrum from the ultraviolet to the infrared, although reference has only been made above to operation with ultraviolet. But, when the apparatus is occupied by a gas under high pressure (10 to 20 bars), it may be more advantageous to use the light produced in the red and the infrared.

We claim:

1. An imaging process for detecting and localizing incident neutral radiations, comprising the steps of:
    subjecting a body of gas to said radiations through collimator means under conditions which result in electron formation upon absorption of the radiations by the gas;
    drifting the electrons toward a photon production space by an electric field;
    subjecting said photon production space to an electric field of sufficient value to produce secondary photons by excitation of atoms of said gas in said space by said electrons;
    receiving said secondary photons on a layer of wavelength shifter material located on an output window retaining said body of gas, and simultaneously determining the locations of light flashes on said layer and the energy of said light flashes.

2. A process according to claim 1, wherein the electrons are drifted by a parallel electric field whose value has an order of magnitude in the 100 V/cm range.

3. A process according to claim 1, wherein the electrons are drifted by a field of about 500 V/cm.

4. A process according to any one of claims 1-3, wherein the electric field in the photon production space has an order of magnitude in the kV/cm range.

5. A imaging process for detecting and localizing incident X or soft gamma radiations comprising the steps of
    subjecting a body of gas to said radiations through a pin hole collimator under conditions which result in electron formation upon absorption of the radiations by the gas;
    drifting the electrons toward a photon production space by an electric field;
    subjecting said photon production space to an electric field of sufficient value to produce secondary photons by excitation of atoms of said gas in said space by said electrons;
    detecting the formation of said secondary photons and determining the location of such formation;
    detecting the light event associated with each said electron formation and measuring time elapsed between said light event and the secondary photon formation 31.

6. An imaging system for determining the distribution of neutral radiation from a source, comprising:

a gas filled enclosure having an input window impervious to light and transparent to said radiation and an output window transparent to light, the atoms of said gas being adapted to produce photoelectrons by interaction with said neutral radiation;

collimator means for location on the path of said radiation between said source and input window;

parallel electrode means transparent to said radiation, located in said enclosure and associated with electric supply means for defining in said enclosure an interaction and electron drift space and a secondary photon production space, said electrode means and electrical supply means being arranged for drifting the electrons formed in the interaction space to the secondary photon production space;

a layer of wavelength shifter material on said output window;

and detection means associated with said layer for simultaneously localizing the light emitting events in said layer and determining their intensity.

7. A system according to claim 6, wherein said detection means comprises energy analyzing means having a predetermined energy window whereby only those events corresponding to said window are localized and displayed.

8. A system according to claim 7, wherein said detection means comprises an array of photomultiplying tubes confronting said layer.

9. A system according to claim 7, further comprising means for providing an electric field in a space separating said output window and said secondary photon production space which has a direction opposite to the field in said secondary photon production space.

* * * * *